Figure 1:
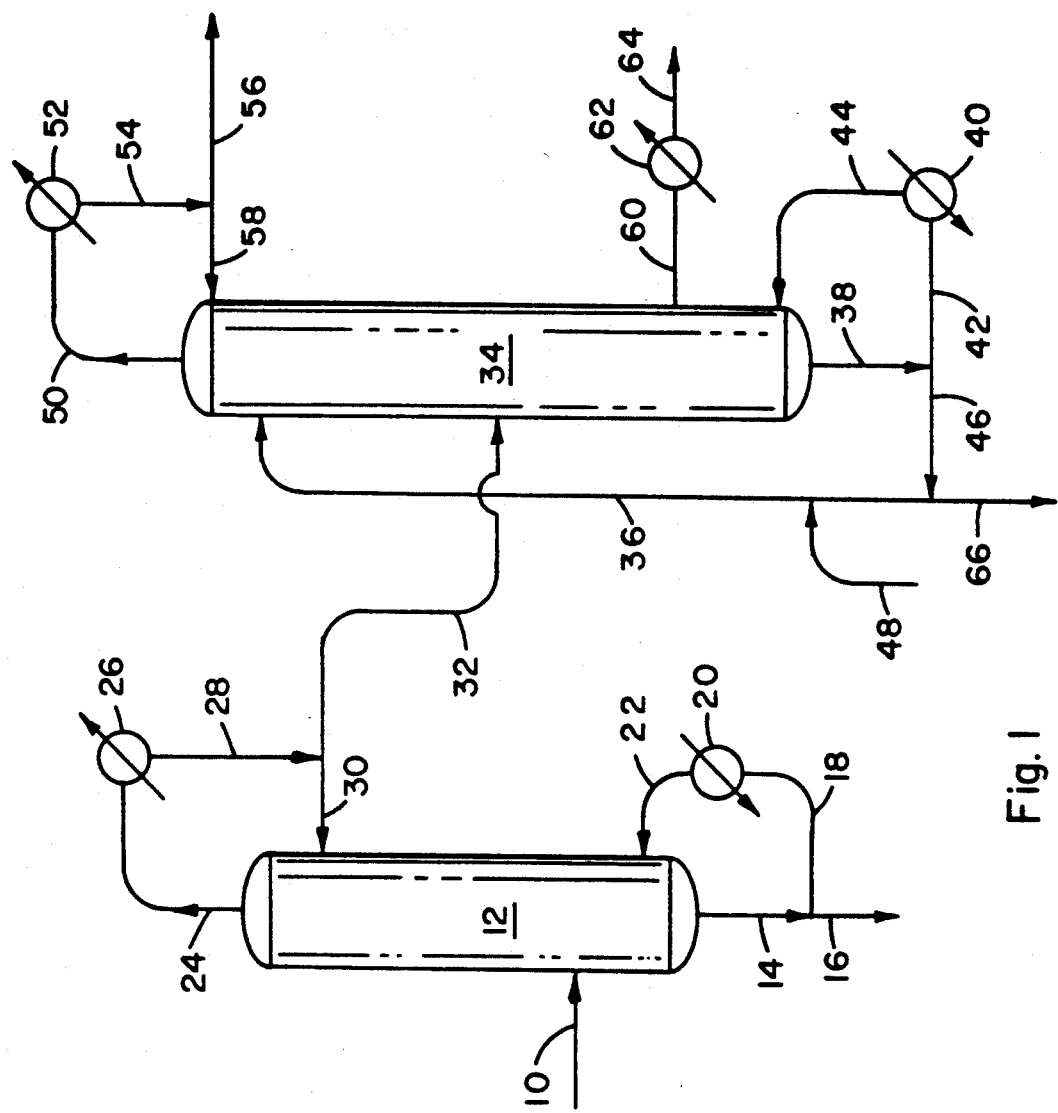

United States Patent [19]
Cook et al.

[11] Patent Number: 5,244,545
[45] Date of Patent: * Sep. 14, 1993

[54] PROCESS FOR REMOVING ACETONE FROM CARBONYLATION PROCESSES

[75] Inventors: Steven L. Cook; Robert M. Schisla, Jr.; Charles E. Outlaw; Joseph R. Zoeller, all of Kingsport, Tenn.

[73] Assignee: Eastman Kodak Company, Rochester, N.Y.

[*] Notice: The portion of the term of this patent subsequent to Oct. 15, 2008 has been disclaimed.

[21] Appl. No.: 774,023

[22] Filed: Oct. 9, 1991

[51] Int. Cl.$^5$ .................. B01D 3/40; C07C 45/83; C07C 51/12

[52] U.S. Cl. .................. 203/83; 203/95; 203/96; 203/DIG. 19; 562/891; 562/898; 568/387; 568/411

[58] Field of Search .................. 203/83, 76, 95, 96, 203/DIG. 19; 568/411, 387; 562/891, 898

[56] References Cited

U.S. PATENT DOCUMENTS

| | | | |
|---|---|---|---|
| 2,662,848 | 12/1953 | Emerson et al. | 568/411 |
| 3,031,384 | 4/1962 | Sirois et al. | 568/411 |
| 3,409,513 | 11/1968 | Hamlin et al. | 203/46 |
| 3,531,376 | 9/1970 | Minoda et al. | 203/33 |
| 3,672,961 | 6/1972 | Nixon | 568/411 |
| 3,686,078 | 8/1972 | Hauptmann et al. | 568/411 |
| 4,046,807 | 9/1977 | Kuckertz | 260/549 |
| 4,252,748 | 2/1981 | Hoch et al. | 568/411 |
| 4,374,070 | 2/1983 | Larkins et al. | 260/549 |
| 4,444,624 | 4/1984 | Erpenbach et al. | 203/61 |
| 4,559,183 | 12/1985 | Hewlett | 260/546 |
| 4,717,454 | 1/1988 | Erpenbach et al. | 203/29 |
| 4,722,769 | 2/1988 | Chan et al. | 568/411 |
| 5,057,192 | 10/1991 | Zoeller et al. | 203/DIG. 19 |

FOREIGN PATENT DOCUMENTS

0074506 3/1983 European Pat. Off. .

Primary Examiner—Wilbur Bascomb, Jr.
Attorney, Agent, or Firm—J. Frederick Thomsen; William P. Heath, Jr.

[57] ABSTRACT

Disclosed is an improved process for the removal of acetone from a production system wherein acetic anhydride is produced by contacting a mixture comprising methyl iodide and methyl acetate and/or dimethyl ether with carbon monoxide in the presence of a carbonylation catalyst or catalyst system. The process comprises two distillation steps wherein acetone is separated from a mixture of methyl acetate, methyl iodide and acetone.

9 Claims, 2 Drawing Sheets

PROCESS FOR REMOVING ACETONE FROM CARBONYLATION PROCESSES

This invention pertains to a process of removing acetone formed during the production of acetic anhydride or a mixture of acetic anhydride and acetic acid by carbonylation processes.

The preparation of acetic anhydride by contacting a mixture comprising methyl iodide and methyl acetate and/or dimethyl ether with carbon monoxide in the presence of a rhodium catalyst has been reported extensively in the patent literature. See, for example, U.S. Pat. Nos. 3,927,078, 4,046,807, 4,374,070 and 4,559,183 and European Patents 8396 and 87,870. These patents disclose that the reaction rate can be increased if the catalyst system includes a promoter such as certain amines, quaternary ammonium compounds, phosphines and inorganic compounds such as lithium compounds. The crude or partially-refined product obtained from such acetic anhydride processes typically comprises a mixture of acetic anhydride and acetic acid as a result of the use of acetic acid as a process solvent and/or the co-production of acetic acid by including methanol and/or water in the feed to the carbonylation reactor.

Acetone is formed in the above-described carbonylation process but since it accumulates in the acetic anhydride production system to a maximum level of about 5 weight percent, based on the total weight of the contents of the carbonylation reactor, its removal is not essential to the operation of the manufacturing system. Furthermore, the value of the relatively small amount of acetone formed is not sufficient to justify the cost of its separation and purification to a sales grade acetone product. Although the mechanism by which acetone achieves a maximum steady state concentration is not known, it generally has been assumed that it is consumed in the formation of process "tars".

A number of acetone removal processes have been described in the patent literature although there has been no apparent economic incentive for using them. U.S. Pat. No. 4,252,748 describes a complex procedure in which all of the methyl iodide, all of the acetone, and some methyl acetate is removed from a low-boiling, recycle stream. The stream is then fractionated to obtain a methyl acetate-acetone rich stream which is then subjected to an azeotropic distillation with pentane, yielding methyl acetate and an acetone-containing pentane stream. The acetone is extracted with water and the pentane is recycled. This complex scheme requires the processing of large volumes of effluent and entails a total of 5 operational steps (4 distillations and an extraction). Furthermore, one would expect that a portion of the methyl iodide, the most valuable process material in this stream, would accumulate in the pentane.

U.S. Pat. No. 4,444,624 describes a system similar to the process of the '748 patent wherein a portion of the low boiler effluent is distilled with a countercurrent of acetic acid to give a fraction rich in methyl iodide and methyl acetate and a second fraction rich in methyl acetate and acetone, both of which contain very large quantities of acetic acid. The acetone-containing fraction is further distilled to give a fraction containing primarily methyl acetate and most of the acetone. The ratio of methyl acetate to acetone is very high, generally about 50:1. The acetone is removed from the larger amount of methyl acetate by azeotropic distillation with pentane and subsequent aqueous extraction to remove the acetone. This process employs very large volumes of acetic acid, generally around 1 part of acetic acid for every 2 parts of low-boiler fraction to be extractively distilled, and entails 4 operational steps (3 distillations and extraction.) This process requires one less step than the process of the '748 patent only because it does not attempt to purify the acetone from the acetone-water mixture. The processes of both the '748 and '624 patents require the use of pentane which introduces the risk of product contamination since pentane is not otherwise used in the acetic anhydride production system.

Finally, according to U.S. Pat. No. 4,717,454, acetone may be removed by converting it to condensation products which may be removed from the production system in the distillation as part of the ethylidene diacetate.

The process of the present invention provides for the removal of acetone from a production system in which acetic anhydride is produced by contacting carbon monoxide with a mixture comprising methyl iodide and methyl acetate and/or dimethyl ether in the presence of a catalyst system and acetic acid by means of the steps comprising:

(1) obtaining from the production system a low-boiling stream comprising methyl acetate, methyl iodide, acetic acid and acetone;

(2) distilling the stream of Step (1) to obtain:
  (a) an overhead stream comprising methyl acetate, methyl iodide and acetone; and
  (b) an underflow stream comprising methyl acetate, methyl iodide, acetone and essentially all of the acetic acid;

(3)
  (a) feeding the Step (2)(a) stream to the middle section of a distillation column; and
  (b) feeding water to the upper section of the distillation column; or,
  instead of steps (3)(a) and (3)(b),
  (c) feeding water to the Step (2)(a) stream and feeding the resulting mixture to the middle section of a distillation column; and (4) removing from the distillation column:
  (a) an overhead vapor stream comprising methyl iodide and methyl acetate;
  (b) an underflow liquid stream comprising water; and
  (c) a vapor stream comprising acetone and water from the lower section of the distillation column; or,
  instead of streams (4)(b) and (4)(c),
  (d) an underflow liquid stream comprising water and acetone.

The process of the present invention provides a means for the removal of acetone using a minimum of steps and processing equipment without the loss of any significant amounts of materials in the acetone disposal stream. Operation of the described acetone removal process results in a decrease in the amount of acetone present in the carbonylation reactor, e.g., acetone concentrations of about 2.0 to 2.5 weight percent based on the total weight of the reactor contents. Operation of the carbonylation process in the presence of lower levels of acetone results in the production of acetic anhydride containing lower levels of "reducing substances." One of the purity specifications for acetic anhydride which is difficult to achieve is the level of "reducing substances", a specification which is particularly important to manufacturers of cellulose acetate. A typical specification requires a permanganate reducing substances test value of at least 30 minutes according to a modification of the Substances Reducing Permanganate Test, American Chemical Society Specifications published in Reagent Chemicals, 6th Ed., American Chemical Society, Washington, D.C., pp. 66 and 68. The use of acetic anhydride containing lower levels of reducing substances decreases the amount of bleaching agents required in cellulose acetate manufacturing processes, thus lowering the manufacturing costs and further enhancing the value of the acetic anhydride. The process provided by our invention provides a means for producing, by the carbonylation processes described above, acetic anhydride which will more consistently pass the reducing substances test.

Figure 2:
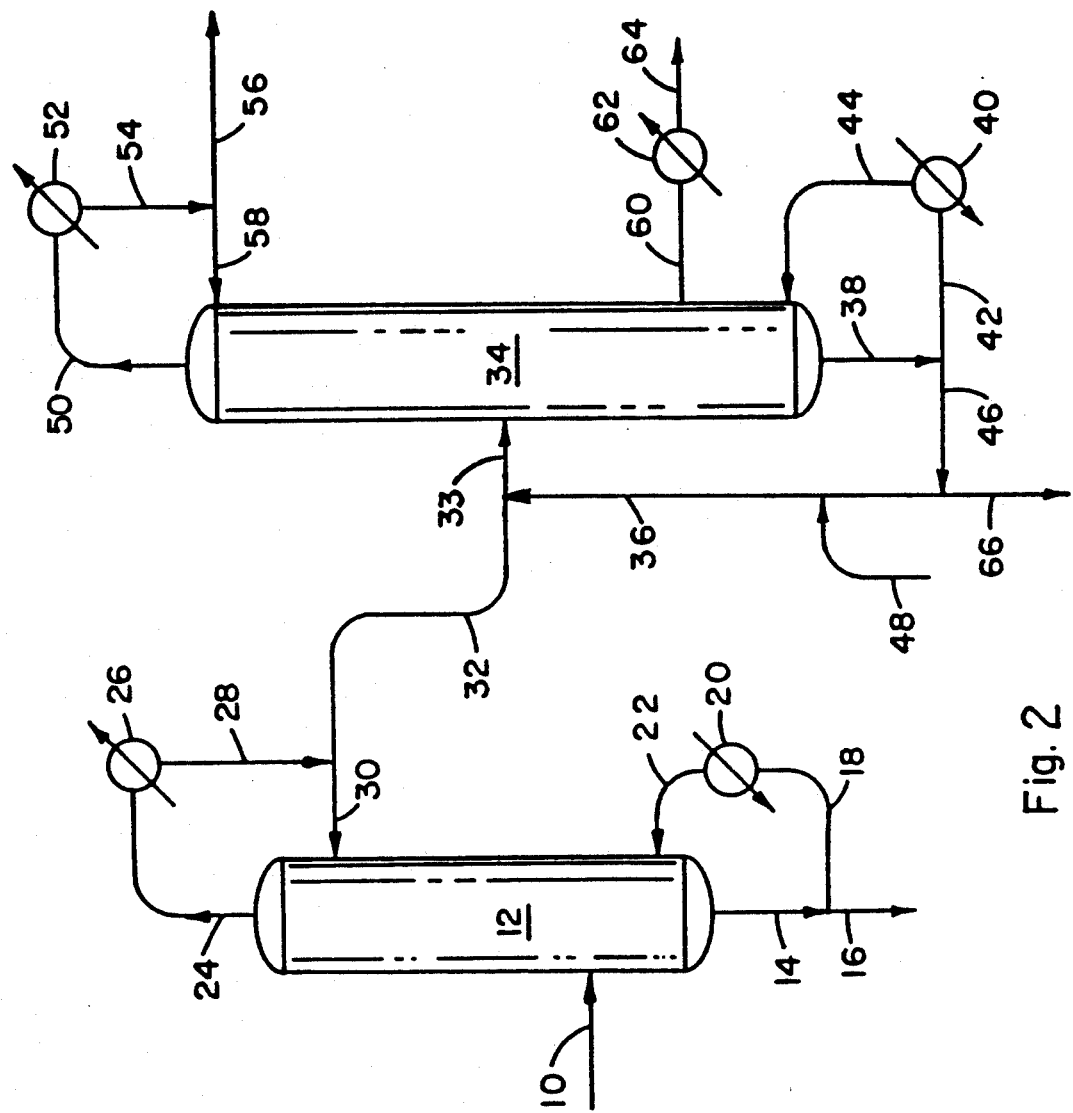

The accompanying FIGS. 1 and 2 are process flow diagrams illustrating a plurality of systems embodying the principles of the process of the present invention. It is, of course, possible that the acetone removal process may be operated by modifying the specific processes illustrated by the Figures. The boiling points (°C.) of the volatile materials employed in the process are:

| Material | B.P. |
|---|---|
| MeI | 42.5 |
| Acetone | 56.2 |
| MeOAc | 57.0 |
| MeI/Acetone | 42.4 |
| MeI/MeOAc | 42.1 |
| MeOAc/Acetone | 55.8 | wherein MeI is methyl iodide, MeOAc is methyl acetate, and MeI/Acetone, MeI/MeOAc and MeOAC/Acetone are constant boiling mixtures (binary azeotropes) consisting of, by weight, 95% methyl iodide and 5% acetone, 97.3% methyl iodide and 2.7 methyl acetate, and 50% methyl acetate and 50% acetone, respectively.

Referring to both of FIGS. 1 and 2, a low-boiling mixture comprising methyl acetate, methyl iodide, acetic acid and acetone is fed by conduit 10 to distillation column 12. The low boiling mixture may be obtained from the acetic anhydride production system described in Example 1 of U.S. Pat. No. 4,374,070, as well as other acetic anhydride manufacturing processes. The low boiling mixture is the portion of the reactor effluent remaining after removal of the catalyst components, a substantial amount of the low boiling components and essentially all of the acetic anhydride and higher boiling by-products. Typically, the low boiling mixture consists of about 75 to 45 weight percent methyl acetate, 30 to 15 weight percent methyl iodide and 20 to 5 weight percent acetic acid with the concentration of the acetone varying from about 12 to 4 weight percent, depending on the length of time the acetone removal process has been operated. The mixture also may contain a trace, e.g., about 0.1 to 0.5 weight percent, of acetic anhydride. While the mixture may contain significant amounts, e.g., 30 to 40 weight percent, of acetic anhydride, our process normally is carried out using a mixture from which substantially all of the acetic anhydride and other high boilers such as ethylidene diacetate have been removed elsewhere in the production system.

Distillation column 12 is operated at ambient pressure, a base temperature of about 60° to 70° C. maintained by a heat source such as reboiler 20, and a top temperature of about 40° to 50° C. to fractionate the low boiling mixture into (1) an overhead stream comprising methyl acetate, methyl iodide and acetone and (2) an underflow stream, i.e., a base product stream, comprising methyl acetate, essentially all of the acetic acid, e.g., at least 95 weight percent of the acetic acid fed to the column, and acetone. The underflow stream is removed from distillation column 12 via conduit 14 and may be recycled by conduit 16 to the carbonylation reactor along with additional methyl acetate, methyl iodide and catalyst components. A portion of the underflow is recycled to the base of column 12 by means of conduit 18, reboiler 20 and conduit 22 to provide the required heat. The primary function of column 12 is to remove all, or essentially all, of the acetic acid from the low boiling mixture. To easily accomplish this objective, a substantial portion of the methyl iodide and acetone fed to column 12 is underflowed with the acetic acid.

The vaporized overhead stream is removed from distillation column 12 by means of conduit 24 and passed through condenser 26 wherein substantially all of the stream is converted to a liquid. A portion of the condensate from condenser 26 may be returned via lines 28 and 30 as reflux to distillation column 12. The remainder of the condensate is fed by means of conduits 28 and 32 to the middle section of distillation column 34. Typical reflux ratios for the condensate (volume of conduit 30:volume of conduit 32) are from about 2:1 to 4:1.

In the embodiments illustrated in FIG. 1, water is fed to the upper section of column 34 through conduit 36 at a rate which gives a volume water feed to volume condensate feed, i.e., the feed through line 32, of at least 0.1. Typically, the water:condensate volume ratio of the feed streams to column 34 is in the range of about 1:1 to 8:1, depending on the particular mode in which the distillation column is operated. Column 34 usually contains means such as trays or packing material which provide good mass transfer within the column. For example, column 34 may be equipped with at least 20 trays, typically 25 to 50 trays, to permit separation of acetone from the condensate feed.

In the operation of the distillation, a vapor phase containing primarily methyl acetate and methyl iodide with minor amounts of water and acetone accumulates in the upper portion of column 34 and is removed at or near the top of the column 34 through conduit 50. The vapor of conduit 50 is condensed by heat exchanger 52 and returned to the carbonylation process by means of conduits 54 and 56. A portion of the condensate from heat exchanger 52 may be returned to column 34 via conduits 54 and 58 at a point near the top.

FIG. 1 illustrates two means for removing a stream comprising acetone and water from column 34 for disposal. In one mode of operation, a liquid phase consisting essentially of water containing a minute amount of acetone collects at the bottom of column 34 and is removed as an underflow through conduit 38. A portion of the aqueous underflow is fed to heat source 40 by conduit 42 and recycled to the base of the column via conduit 44 to maintain a base temperature of about 98° to 104° C. The remainder of the liquid phase is recycled by means of conduits 46 and 36 to the upper section of distillation column 34. Fresh water is added as necessary through line 48. An aqueous acetone phase in the form of a second vapor phase consisting essentially of water and acetone, typically at least 80 weight percent of the acetone fed via conduit 32, accumulates in the lower section of column 34. The aqueous acetone phase is removed as a second stream of vapor from the lower portion of column 34 by conduit 62, condensed in condenser 62 and transported by conduit 64 to a suitable industrial waste treatment plant.

In the second means for removing an acetone/water mixture from column 34 according to the process flow diagram constituting FIG. 1, the vapor take-off via line 60 is not employed. Instead, a liquid phase comprising acetone and water is removed from the base of column 34 by means of conduits 38 and removed from the system through conduits 46 and 66. In this mode of operation, the base of column 34 is maintained at about 90° to 95° C., for example by heat source 40 as described previously. Since more water is removed from the system via line 66 in this alternative mode of operation, the amount of fresh water supplied by conduit 48 is increased significantly. A portion of the liquid phase transported by line 46 may be recycled to column 34 by line 36.

The second mode of operation (wherein the vapor take-off via line 60 is not employed) advantageously is utilized when the volume ratio of (i) water fed by conduit 36 to (ii) condensate fed by 32 is relatively low, e.g., from about 0.1:1 to 1:1. When using such low water:condensate ratios, all or substantially all of the liquid phase comprising acetone and water is withdrawn from the acetone removal system via lines 38, 46 and 66. Although the two modes of removing an acetone/water mixture have been described as separate operations, it may be possible to practice the process by means of a combination of vapor take-off via line 60 and liquid take-off via line 66.

Typical compositions of the materials transported by conduits and lines in the operation of the process depicted in FIG. 1 wherein an aqueous acetone vapor is removed via conduit 60 are given below wherein the methyl acetate (MeOAc), methyl iodide (MeI), acetic acid (HOAc), acetone and water components of each stream are given as weight percentages based on the total weight of the stream.

The embodiments of the invention depicted in FIG. 2 differ from the process described hereinabove for FIG. 1 only in the manner in which water is supplied to distillation column 34. In the operation of the processes illustrated by FIG. 2, water is fed via line 36 and combined with the condensate contained in and transported by conduit 32. The water/condensate mixture is fed by means of conduit 33 to the middle section of column 34. The volume ratio of water:condensate comprising the mixture fed to the column may be from about 0.03:1 to as high as 8:1. In all other respects, the column 34 distillation is carried out as described hereinabove.

The acetone removal process of the present invention involves two distillation operations, the first of which comprises the steps of:

(1) obtaining from the production system a low-boiling stream comprising methyl acetate, methyl iodide, acetic acid and acetone;
(2) distilling the stream of Step (1) to obtain:
  (a) an overhead stream comprising methyl acetate, methyl iodide and acetone; and
  (b) an underflow stream comprising methyl acetate, methyl iodide, acetone and essentially all of the acetic acid.

The second distillation, utilizing the overhead stream of Step (2)(a) described above and water, may be carried out by a plurality of combination of steps including:

I (FIG. 1)

(3)
  (a) feeding the Step (2)(a) stream to the middle section of a distillation column; and
  (b) feeding water to the upper section of the distillation column; and
(4) removing from the distillation column:
  (a) an overhead vapor stream comprising methyl iodide and methyl acetate;
  (b) an underflow liquid stream comprising water; and
  (c) a vapor stream comprising acetone and water from the lower section of the distillation column.

II (FIG. 1)

(3)
  (a) feeding the Step (2)(a) stream to the middle section of a distillation column; and
  (b) feeding water to the upper section of the distillation column; and
(4) removing from the distillation column:
  (a) an overhead vapor stream comprising methyl iodide and methyl acetate; and
  (b) an underflow liquid stream comprising water and acetone.

III (FIG. 2)

(3)
  (a) feeding water to the Step (2)(a) stream; and
  (b) feeding the mixture of Step (3)(a) to the middle section of a distillation column; and
(4) removing from the distillation column:
  (a) an overhead vapor stream comprising methyl odide and methyl acetate; and
  (b) an underflow liquid stream comprising water; and
  (c) a vapor stream comprising acetone and water from the lower section of the distillation column.

IV (FIG. 2)

(3)
  (a) feeding water to the Step (2)(a) stream; and
  (b) feeding the mixture of Step (3)(a) to the middle section of a distillation column; and
(4) removing from the distillation column:
  (a) an overhead vapor stream comprising methyl iodide and methyl acetate; and
  (b) an underflow liquid stream comprising water and acetone.

As mentioned previously, the second distillation may employ a combination of two or more of the operations described above.

Typical compositions of the materials transported by conduits and lines in the operation of the processes depicted in FIGS. 1 and 2 are given in Tables 1 and 2 wherein the methyl acetate (MeOAc), methyl iodide (MeI), acetic acid (HOAc), acetone and water components of each stream are given as weight percentages based on the total weight of the stream. Table 1 refers to the process of FIG. 1 wherein an aqueous acetone vapor is removed via conduit 60. Table 2 refers to the process of FIG. 2 wherein an aqueous acetone vapor is not removed via conduit 60 and the volume ratio of water:condensate of the stream transported by line 33 is in the range of 0.1 to 1.1.

TABLE 1

| Conduit | Components | | | | |
| --- | --- | --- | --- | --- | --- |
|  | MeOAc | MeI | HOAc | Acetone | Water |
| 16 | 30–90 | 10–40 | 1–25 | 1–20 | 0 |
| 32 | 3–15 | 75–98 | 0–1 | 0.5–6 | 0–1 |
| 38 | 0–1 | 0–0.5 | 0–0.5 | 0–1 | 97–100 |

TABLE 1-continued

| Conduit | Components | | | | |
|---|---|---|---|---|---|
| | MeOAc | MeI | HOAc | Acetone | Water |
| 56 | 1-15 | 85-98 | 0-0.5 | 0-1 | 0.5-3 |
| 64 | 0-5 | 0-5 | 0-0.5 | 10-40 | 50-80 |

TABLE 2

| Conduit | Components | | | | |
|---|---|---|---|---|---|
| | MeOAc | MeI | HOAc | Acetone | Water |
| 16 | 30-90 | 10-40 | 1-25 | 1-20 | 0 |
| 32 | 3-15 | 75-98 | 0-1 | 0.5-6 | 0-1 |
| 38 | 0-10 | 0 | 0-0.5 | 1-30 | 60-99 |
| 56 | 1-15 | 85-98 | 0-0.5 | 0-1 | 0.5-3 |

The process of the present invention may be employed continuously or semi-continuously as necessary to lower the concentration of the acetone in the carbonylation reactor within a predetermined range. As mentioned hereinabove, operation of the carbonylation process with reduced concentrations of acetone permits the production of acetic anhydride of higher quality with respect to the reducing substances specification. We also have found that such lower acetone concentrations result in an increased production rate, an improvement in the color of the acetic anhydride product, a lowered tar formation rate and a decrease in the tendency of the tar formed to bind rhodium. At least a portion of the production rate increase is due simply to the reactor volume made available for more reactants by the lower volume of acetone present. For example, lowering the acetone level to about 1.4 weight percent as described herein results in about 2% increase in production rate due to increased useful reactor volume.

A reduction in the amount of tar produced by the carbonylation process requires the processing of lower amounts of catalyst-tar mixtures, e.g., as described in U.S. Pat. No. 4,388,217 and 4,945,075, which reduces significantly the risk of rhodium losses in such processes. Due to the cost of rhodium which has risen dramatically, any process improvements which reduce the risk of its loss in the overall acetic anhydride production system have become increasingly important.

The following example illustrates the operation of our novel process in conjunction with the acetic anhydride production system described in U.S. Pat. No. 4,374,070 wherein a mixture of methyl iodide and methyl acetate is contacted with carbon monoxide in the presence of a catalyst system comprising rhodium and a lithium salt at a temperature of about 160° to 220° C. and about 21.7 to 83.7 bar absolute (about 300 to 1200 psig). In the carbonylation process, a feed mixture containing methyl acetate is continuously fed to a carbonylation reactor and a reaction product mixture containing acetic anhydride is continuously removed. The feed to the reactor is such as to maintain within the reaction mixture about 500 to 1000 ppm rhodium, about 1500 to 3700 ppm lithium, about 7 to 35 weight percent methyl iodide and about 5 to 40 weight percent acetic acid.

The effluent from the liquid phase carbonylation reactor is processed to remove therefrom unreacted carbon monoxide and other non-condensible gases and catalyst components. Any dimethyl ether fed to the carbonylation reactor which is not converted to methyl acetate is removed as a component of the non-condensible gases. The remainder of the effluent then is fed to a distillation column from which a crude acetic anhydride/acetic acid mixture is obtained. The vaporized low boiler stream removed at or near the top of the distillation column comprises methyl acetate, methyl iodide, acetic acid and acetone. The low boiler stream is condensed and all or a portion, typically about 5 to 25 weight percent, of it is subjected to the acetone removal process.

At the commencement of the operation of the acetone removal process, the concentration of the acetone in the reactor was 4.0 to 4.5 weight percent. All parts given are by volume.

In accordance with the flow diagram of the Figure, the above-described low boiler stream is fed at a rate of 16 parts per minute via conduit 10 to the lower, mid-section of distillation column 12 operated at a base temperature of 60° to 65° C. to give an acetic acid underflow stream removed by means of line 14. The vapor removed from the top of column 12 is condensed and the condensate fed at 1.75 parts per minute at approximately the mid point of distillation column 34 which is equipped with 45 trays. Water is fed by conduit 36 at 12.2 parts per minute to column 34 at the level of the fortieth tray (tray number 40 from the bottom of the column).

A liquid phase consisting essentially of water is removed from the base of the column by conduit 38 and a portion is recycled through conduit 42, heat source 40 and conduit 44 to the base of the column to maintain a column base temperature of 98° to 104° C. The remainder of the liquid phase underflow is recycled via conduits 38, 46 and 36 to the column.

An upper vapor phase is removed from the top of column 34 by means of conduit 50, condensed in condenser 52 and the condensate is recycled at a rate of 1.7 parts per minute by conduits 54 and 56 to the acetic anhydride production system. A lower vapor phase is removed from the lower section of column 34 at the tray number 5 level by conduit 60, condensed in condenser 62 and disposed of through conduit 64 at the rate of 0.16 parts per minute.

The compositions of the streams transported by conduits 32, 56 and 64 in this example of the operation of the process are given below wherein the methyl acetate (MeOAc), methyl iodide (MeI), acetic acid (HOAc), acetone and water components of each stream are given as weight percentages based on the total weight of the streams.

| Conduit | Components | | | | |
|---|---|---|---|---|---|
| | MeOAc | MeI | HOAc | Acetone | Water |
| 32 | 14.0 | 82.5 | 0 | 3.0 | 0.5 |
| 56 | 5.8 | 93.0 | 0 | 0.0 | 1.2 |
| 64 | 1.0 | 0 | 0 | 29.0 | 70.0 |

The invention has been described in detail with particular reference to preferred embodiments thereof, but it will be understood that variations and modifications can be effected within the spirit and scope of the invention.

We claim:

1. Process for the removal of acetone from a production system in which acetic anhydride is produced by contacting carbon monoxide with a mixture comprising methyl iodide and methyl acetate and/or dimethyl ether in the presence of a catalyst system and acetic acid by means of the steps comprising:

(1) obtaining from the production system a low boiling stream comprising methyl acetate, methyl iodide, acetic acid and acetone;
(2) distilling the stream of Step (1) to obtain:
   (a) an overhead stream comprising methyl acetate, methyl iodide and acetone; and
   (b) an underflow stream comprising methyl acetate, methyl iodide, acetone and essentially all of the acetic acid;
(3)
   (a) feeding the Step (2)(a) stream to the middle section of a distillation column; and
   (b) feeding water to the upper section of the distillation column; or,
   instead of steps (3)(a) and (3)(b),
   (c) feeding water to the Step (2)(a) stream and feeding the resulting mixture to the middle section of a distillation column; and
(4) removing from the distillation column:
   (a) an overhead vapor stream comprising methyl iodide and methyl acetate;
   (b) an underflow liquid stream comprising water; and
   (c) a vapor stream comprising acetone and water from the lower section of the distillation column; or, instead of streams (4)(b) and (4)(c),
   (d) an underflow liquid stream comprising water and acetone.

2. Process according to claim 1 comprising the steps of:
(1) obtaining from the production system a low boiling stream comprising methyl acetate, methyl iodide, acetic acid and acetone;
(2) distilling the stream of Step (1) to obtain:
   (a) an overhead stream comprising methyl acetate, methyl iodide and acetone; and
   (b) an underflow stream comprising methyl acetate, methyl iodide, acetone and essentially all of the acetic acid;
(3)
   (a) feeding the Step (2)(a) stream to the middle section of a distillation column; and
   feeding water to the upper section of the distillation column; and
(4) removing from the distillation column:
   (a) an overhead vapor stream comprising methyl iodide and methyl acetate;
   (b) an underflow liquid stream comprising water; and
   (c) a vapor stream comprising acetone and water from the lower section of the distillation column.

3. Process according to claim 2 wherein the volume ratio of the Step (3)(b) feed to the Step (3)(a) stream is about 1:1 to 8:1.

4. Process according to claim 1 comprising the steps of:
(1) obtaining from the production system a low boiling stream comprising methyl acetate, methyl iodide, acetic acid and acetone;
(2) distilling the stream of Step (1) to obtain:
   (a) an overhead stream comprising methyl acetate, methyl iodide and acetone; and
   (b) an underflow stream comprising methyl acetate, methyl iodide, acetone and essentially all of the acetic acid;
(3)
   (a) feeding the Step (2)(a) stream to the middle section of a distillation column; and
   (b) feeding water to the upper section of the distillation column; and
(4) removing from the distillation column:
   (a) an overhead vapor stream comprising methyl iodide and methyl acetate; and
   (b) an underflow liquid stream comprising water and acetone.

5. Process according to claim 4 wherein the volume ratio of the Step (3)(b) feed to the Step (3)(a) stream is about 0.1:1 to 1:1.

6. Process according to claim 1 comprising the steps of:
(1) obtaining from the production system a low boiling stream comprising methyl acetate, methyl iodide, acetic acid and acetone;
(2) distilling the stream of Step (1) to obtain:
   (a) an overhead stream comprising methyl acetate, methyl iodide and acetone; and
   (b) an underflow stream comprising methyl acetate, methyl iodide, acetone and essentially all of the acetic acid;
(3)
   (a) feeding water to the Step (2)(a) stream; and
   (b) feeding the mixture of Step (3)(a) to the middle section of a distillation column; and
(4) removing from the distillation column:
   (a) an overhead vapor stream comprising methyl iodide and methyl acetate; and
   (b) an underflow liquid stream comprising water; and
   (c) a vapor stream comprising acetone and water from the lower section of the distillation column.

7. Process according to claim 6 wherein the volume ratio of the Step (3)(b) feed to the Step (3)(a) stream is about 1:1 to 8:1.

8. Process according to claim 1 comprising the steps of:
(1) obtaining from the production system a low boiling stream comprising methyl acetate, methyl iodide, acetic acid and acetone;
(2) distilling the stream of Step (1) to obtain:
   (a) an overhead stream comprising methyl acetate, methyl iodide and acetone; and
   (b) an underflow stream comprising methyl acetate, methyl iodide, acetone and essentially all of the acetic acid;
(3)
   (a) feeding water to the Step (2)(a) stream; and
   (b) feeding the mixture of Step (3)(a) to the middle section of a distillation column; and
(4) removing from the distillation column:
   (a) an overhead vapor stream comprising methyl iodide and methyl acetate; and
   (b) an underflow liquid stream comprising water and acetone.

9. Process according to claim 6 wherein the volume ratio of the Step (3)(b) feed to the Step (3)(a) stream is about 0.03:1 to 1:1.

* * * * *

UNITED STATES PATENT AND TRADEMARK OFFICE
CERTIFICATE OF CORRECTION

PATENT NO. : 5,244,545

DATED : September 14, 1993

INVENTOR(S) : Steven L. Cook et al.

It is certified that error appears in the above-identified patent and that said Letters Patent is hereby corrected as shown below:

Column 10, line 62 (Claim 9, line 1), "claim 6" should be --- claim 8 ---.

Signed and Sealed this

Twenty-sixth Day of April, 1994

Attest:

BRUCE LEHMAN

*Attesting Officer*    *Commissioner of Patents and Trademarks*